(12) United States Patent
Sikora et al.

(10) Patent No.: US 12,090,058 B2
(45) Date of Patent: Sep. 17, 2024

(54) TIBIAL RESURFACING SYSTEM AND METHOD

(71) Applicant: Arthrosurface, Inc., Franklin, MA (US)

(72) Inventors: George Sikora, Bridgewater, MA (US); Steven W. Ek, Bolton, MA (US)

(73) Assignee: Arthrosurface, Inc., Franklin, MA (US)

( * ) Notice: Subject to any disclaimer, the term of this patent is extended or adjusted under 35 U.S.C. 154(b) by 25 days.

(21) Appl. No.: 17/967,427

(22) Filed: Oct. 17, 2022

(65) Prior Publication Data

US 2023/0110492 A1    Apr. 13, 2023

Related U.S. Application Data

(60) Continuation of application No. 16/854,244, filed on Apr. 21, 2020, now Pat. No. 11,471,289, which is a continuation of application No. 14/133,943, filed on Dec. 19, 2013, now Pat. No. 10,624,752, which is a division of application No. 13/042,382, filed on Mar. 7, 2011, now abandoned, and a continuation-in-part of application No. 11/779,044, filed on Jul. 17, 2007, now abandoned.

(Continued)

(51) Int. Cl.
| | |
|---|---|
| *A61B 17/15* | (2006.01) |
| *A61B 17/16* | (2006.01) |
| *A61B 17/17* | (2006.01) |
| *A61F 2/38* | (2006.01) |
| *A61B 90/00* | (2016.01) |

(52) U.S. Cl.
CPC ............ *A61F 2/389* (2013.01); *A61B 17/157* (2013.01); *A61B 17/1637* (2013.01); *A61B 17/1675* (2013.01); *A61B 17/1764* (2013.01); *A61B 2090/062* (2016.02)

(58) Field of Classification Search
CPC .............. A61B 17/157; A61B 17/1675; A61B 17/1764; A61B 17/8897; A61B 2090/062; A61B 17/1637; A61F 2/30942; A61F 2/389; A61F 2002/30329; A61F 2002/30827; A61F 2002/30878; A61F 2002/3093

See application file for complete search history.

(56) References Cited

U.S. PATENT DOCUMENTS

2008/0015607 A1\* 1/2008 D'Alessio ............. A61F 2/4684
606/87

\* cited by examiner

*Primary Examiner* — Samuel S Hanna
(74) *Attorney, Agent, or Firm* — GOODWIN PROCTER LLP

(57) ABSTRACT

An implant resection system for preparing an implant site to replace a defect in an articular surface of a first bone includes a guide configured to be coupled generally perpendicular to the first bone proximate to the defect. The guide includes a body portion defining a plurality of excision passageways. The excision passageways each define a generally cylindrical core pathway configured to extend generally perpendicular to the first bone which partially overlaps with an adjacent generally cylindrical core pathway. A projection associated with each of the plurality of the generally cylindrical core pathways defines a truncated cylindrical excision site extending through a portion of the articular surface. Each truncated cylindrical excision site partially overlaps with at least one adjacent truncated cylindrical excision site.

18 Claims, 16 Drawing Sheets

Related U.S. Application Data

(60) Provisional application No. 61/310,774, filed on Mar. 5, 2010, provisional application No. 60/807,538, filed on Jul. 17, 2006.

TIBIAL RESURFACING SYSTEM AND METHOD

CROSS REFERENCE TO RELATED APPLICATIONS

This application is a continuation of U.S. patent application Ser. No. 16/854,244, filed Apr. 21, 2020, which is a continuation of U.S. patent application Ser. No. 14/133,943, filed Dec. 19, 2013, which is a division of U.S. patent application Ser. No. 13/042,382, filed Mar. 7, 2011, which claims the benefit of U.S. Provisional Patent Application No. 61/310,774, filed Mar. 5, 2010, which is fully incorporated herein by reference. U.S. patent application Ser. No. 14/133,943 is also a continuation-in-part of U.S. patent application Ser. No. 11/779,044, filed Jul. 17, 2007, which claims the benefit of U.S. Provisional Patent Application Ser. No. 60/807,538, filed Jul. 17, 2006, the entire disclosures of all of which are incorporated fully herein by reference.

FIELD

This disclosure relates to devices and methods for the repair of defects that occur in articular cartilage on the surface of bones, particularly the knee.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF THE DRAWINGS

Features and advantages of the present invention are set forth by description of embodiments consistent with the present invention, which description should be considered in conjunction with the accompanying drawings wherein.

DETAILED DESCRIPTION

By way of summary, one embodiment of the present disclosure may feature a system and method for repairing a portion of the articular surface proximate to a defect. While the present disclosure will be described in terms of a system and method for repairing a portion of the tibial articular surface, it should be understood that the system and method may be used to repair other articular surfaces (such as, but not limited to, femoral articular surfaces and the like). The system and method may include securing a one or more guides/jigs defining one or more passageways to a portion of the tibia (e.g., immediately below the tibial articular surface) proximate to the defect. The passageways may define a generally cylindrical core pathway for a drill bit (i.e., a coring drill bit). When the guide is secured to the femur, the generally cylindrical core pathway may partially intersect/overlap with the articular surface and a portion of the bone beneath the articular surface. A first truncated cylindrical excision site may be formed in the articular surface and/or bone beneath the articular surface by advancing the drill along the core pathway. The drill may have a diameter large enough to remove a portion of the articular surface as it is advanced through the guide and into the articular surface. Additional truncated cylindrical excision sites may also be formed. One or more of the additional truncated cylindrical excision sites may partially overlap with adjacent truncated cylindrical excision sites.

The guide and/or the drill may include a depth feature configured to control the depth of the truncated cylindrical excision site formed in the articular surface/bone. The depth feature may prevent the drill from being advanced too far, thereby preventing the drill from accidentally damaging any structures proximate to the excision sites (e.g., nerves). The system and method may also include an implant having a load bearing surface having a surface contour/geometry based on the surface contour/geometry of the patient's original removed articular surface. For example, the surface contour/geometry of the load bearing surface may be based on one or more measurements taken of the patient's original articular surface. The implant may also feature a bone facing or distal surface having a surface contour/geometry configured to be received in the truncated cylindrical excision sites.

Figure 1:
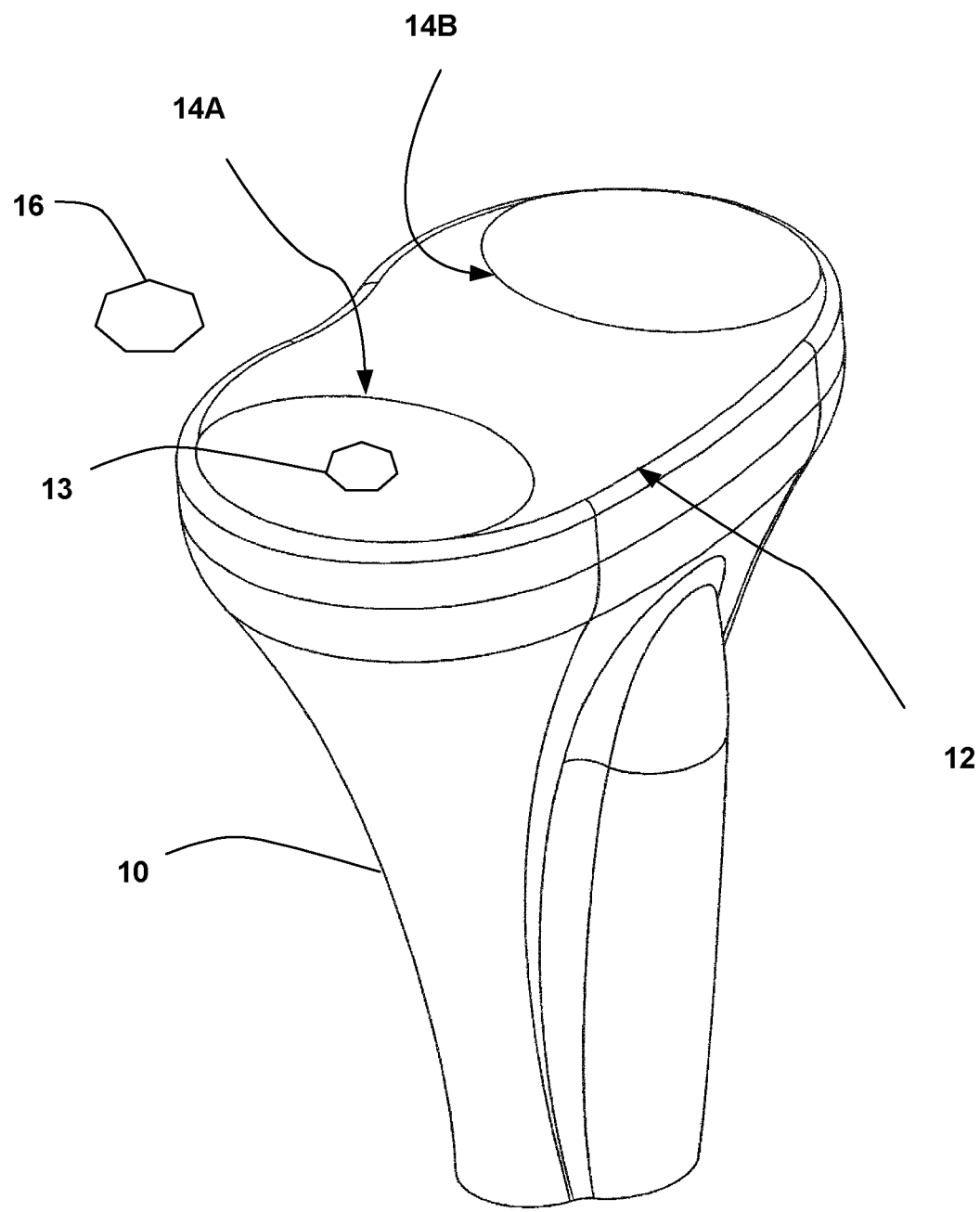
FIG. 1 is a schematic diagram illustrating an incision proximate the knee.

Turning now to FIG. 1, a tibia 10 is generally illustrated. As may be appreciated, the tibial articular surface 12 may include a tibial plateau comprising a plurality of concaved surfaces 14a, 14b configured to articulate with the femoral condyles (not shown for clarity). It may be further appreciated that the tibial articular surface 12 may include additional concaved surfaces not shown for the sake of clarity. One or more of the concaved surfaces (e.g., concaved surface 14a) may include a defect 13 in the tibial articular surface 12 to be repaired. On the distal side of the tibia 10, a nerve bundle 16 is located. As described herein, the system and method according to one embodiment of the present disclosure may be configured to avoid damaging the nerve bundle when forming the excision site(s).

For illustrative purposes, the following will describe a system and method for preparing an implant site comprising three partially overlapping truncated cylindrical excision sites and an implant configured to fit therein. As may be appreciated, the system and method according to the present disclosure may be used to form an implant site having greater than or fewer than three partially overlapping truncated cylindrical excision sites. As will be evident from the following description, the truncated cylindrical excision sites may be formed by drilling along the anterior-posterior plane (i.e., from an anterior face of the tibia 10 and extending generally towards the posterior face of the tibia 10).

Figure 2:
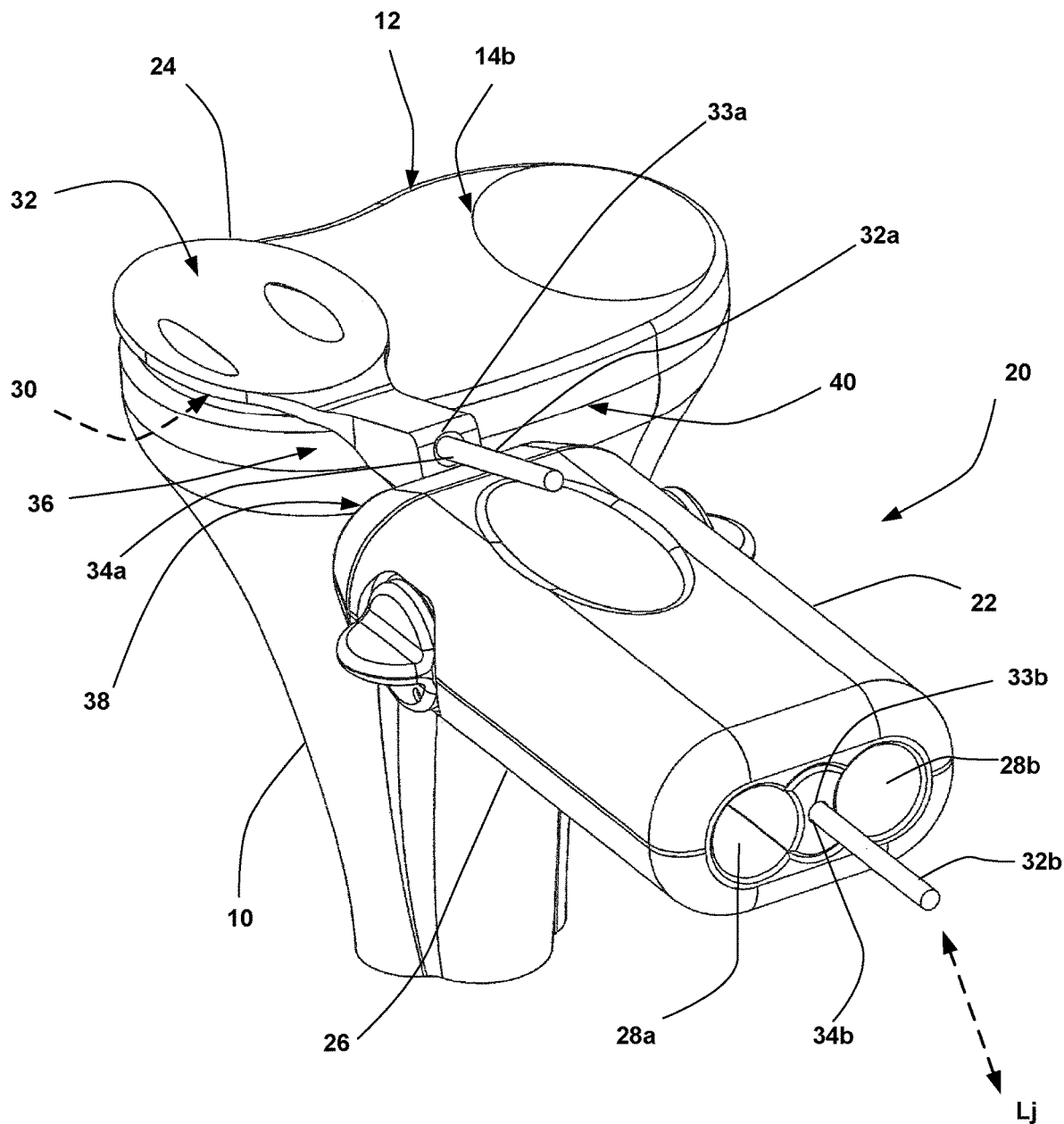
FIG. 2 is a perspective view illustrating one embodiment of a drill guide coupled to the tibia consistent with the present disclosure.

Turning now to FIG. 2, one embodiment of a first guide 20 secured to the tibia 10 is generally illustrated consistent with the present disclosure. The first guide 20 may include a jig 22 and a spoon 24. The jig 22 may include a body portion 26 defining two excision passageways 28a, 28b. As explained herein, the excision passageways 28a, 28b may each define a generally cylindrical core pathway for a drill bit which may be used to form a first and a second truncated cylindrical excision site on the tibial articular surface 12. As shown, the first and the second excision passageways 28a, 28b may be offset relative to each other (i.e., the first and the second excision passageways 28a, 28b may be separated by a distance generally perpendicular to the longitudinal axes of the first and the second excision passageways 28a, 28b such that the first and the second truncated cylindrical excision sites formed in the articular surface 12 do not overlap as described herein).

The position of the jig 22 (and in particular, the excision passageways 28a, 28b) may be set based on, at least in part, the spoon 24. In particular, the spoon 24 may include a generally convex base portion 30 having a surface contour substantially corresponding to the curvature of the concaved surface 14a being repaired (e.g., the concaved surface 14a which has the defect 13). The upper portion 32 of the spoon 24 may have a generally concaved surface (e.g., generally corresponding to the curvature of the concaved surface 14a being repaired). The spoon 24 may have a cross-sectional thickness configured to facilitate advancement of the spoon 24 between the tibial articular surface 12 and the femoral condyles (not shown). For example, the cross-sectional thickness of the spoon 24 may be selected to provide sufficient rigidity to align the jig 22 relative to the tibial articular surface 12 (and in particular, the defect 13 on the concaved surface 14a) while also minimizing the required separation between the tibia 10 and the femur.

The spoon 24 may be an integral component of the jig 22 (e.g., a unitary or single one-piece structure) or may be configured to be releasably coupled to the jig 22. For example, the spoon 24 may include an arm portion 36 configured to extend generally outwardly from a distal face 38 (e.g., a bone facing surface) of the jig 22. The size and shape of the arm portion 36 may be configured to allow a portion of the distal face 38 to be disposed proximate to the perimeter (e.g., proximate to the meniscus 40) when the spoon 24 is disposed on the concaved surface 14a such that the generally cylindrical core pathways associated with the first and second excision passageways 28a, 28b partially overlap with the tibial articular surface 12.

In practice, the first guide 20 may be positioned relative to the defect 13 on the concaved surface 14a by advancing the spoon 24 between the tibial articular surface 12 and the femur such that the base portion 30 of the spoon 24 is disposed over at least a portion of the defect 13 on the tibial articular surface 12. The spoon 24 may be advanced until the distal face 38 of the jig 22 generally abuts against a portion of the tibia 10 (e.g., proximate to the meniscus 40). The size and shape of the base portion 30 as well as the arm portion 36/distal face 38 may be configured to generally center the spoon 24 within the concaved surface 14a.

Once the spoon 24 is positioned over the defect 13, the spoon 24 and the jig 22 may be secured to the tibia 10 using one or more pins 32 or the like extending through one or more locking passageways 34 in the spoon 24 and/or the jig 22. For example, the spoon 24 may include a spoon locking passageway 34a extending through a portion of the spoon 24 (e.g., the arm portion 36) configured to align a pin 32a into the tibial bone beneath the tibial articular surface 12. Alternatively (or in addition), the jig 22 may include a jig locking passageway 34b extending through a portion of the body 26 configured to align a pin 32b into the tibial bone beneath the tibial articular surface 12. While two pins 32a, 32b are shown, it should be appreciated that the first guide 20 may be secured using greater than or fewer than two pins 32a, 32b.

The pins 32a, 32b may include depth feature 33a, 33b configured to control the depth of the pins 32a, 32b in the bone 10 (i.e., to prevent the pins 32a, 32b from being set too deep or too shallow into the bone 10). The depth feature 33a, 33b may comprise an indicia (e.g., but not limited to, a laser marking, groove, or the like) which may be aligned with the proximal end of the passageways 34a, 34b. Pin 32a may extend a smaller distance into the tibia 10 compared to pin 32b.

Figure 3:
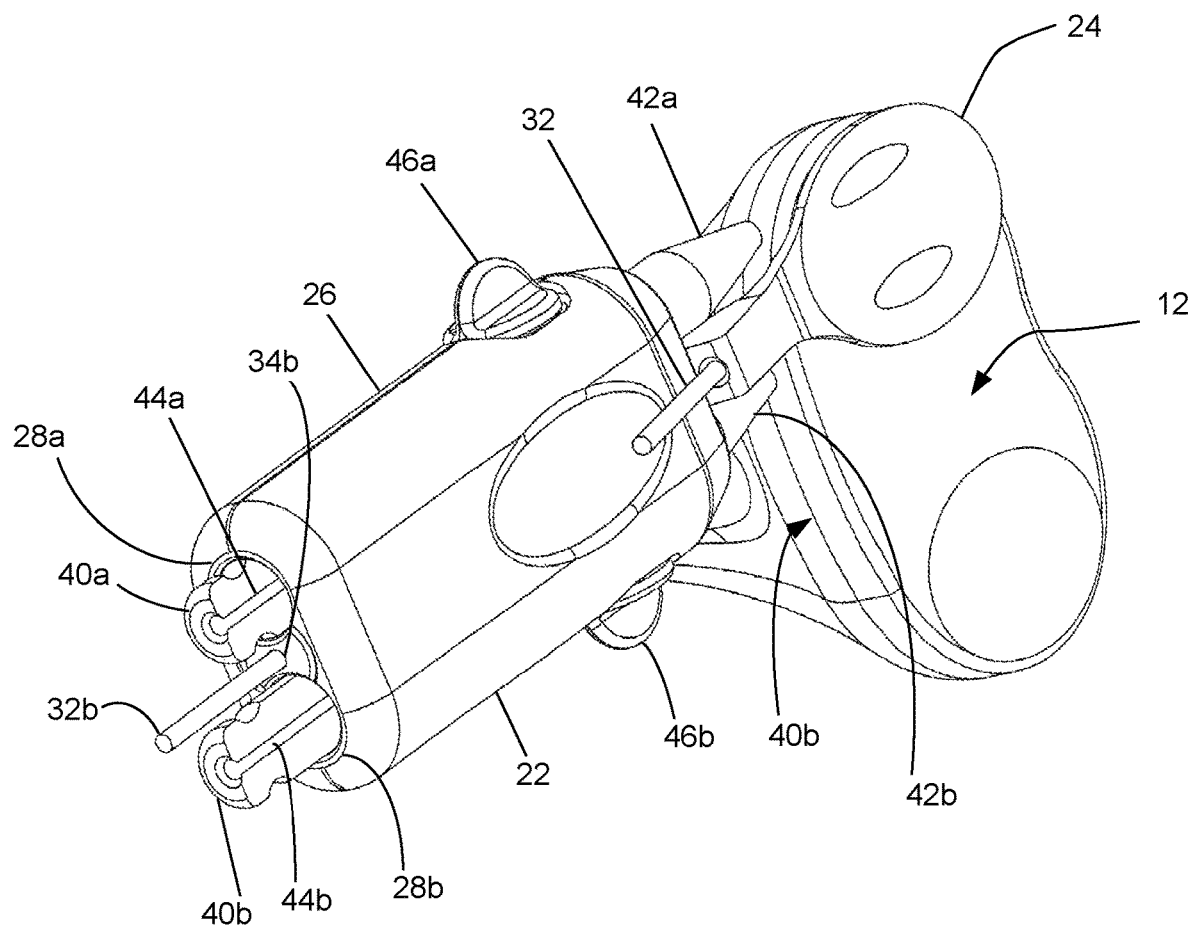
FIG. 3 is a perspective view illustrating dowels advanced within the drill guide consistent with the present disclosure.

Turning now to FIG. 3, the first guide 20 may optionally be secured to the tibia 10 by advancing one or more dowels or bushings 40a, 40b against the bone 10. For example, a first and a second dowel 40a, 40b may be advanced through the first and second excision passageways 28a, 28b, respectively. One or more of the dowels 40a, 40b may feature a tapered tip 42a, 42b and a longitudinally disposed passageway 44a, 44b (a proximal end of the dowels 40a, 40b is shown in cross-section to better illustrate the passageway 44a, 44b). The dowels 40a, 40b may be advanced through the passageways 28a, 28b until the tapered tip 42a, 42b engages against (e.g., abuts) a portion of the tibia 10 (e.g., proximate to the meniscus 40). Once the dowels 40a, 40b abut the tibia 10, the dowels 40a, 40b may be locked into position relative to the jig 22 using locking fasteners 46a, 46b. The locking fasteners 46a, 46b may include, but are not limited to, a set screw, biased tab, ratchet mechanism, or the like.

Figure 4:
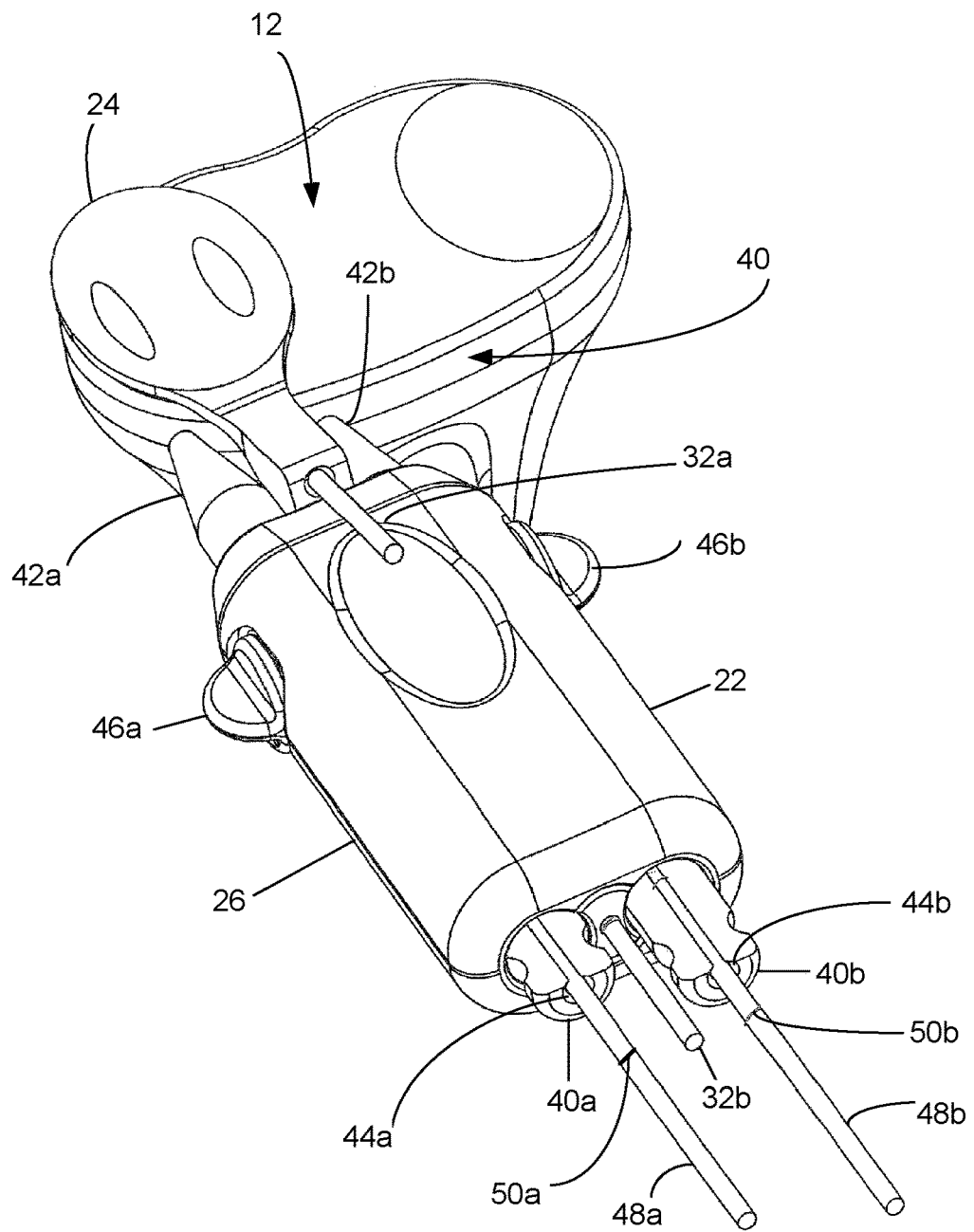
FIG. 4 is a perspective view illustrating pin advanced within the dowels in the drill guide consistent with the present disclosure.

Alignment pins 48a, 48b may be advanced through the passageways 44a, 44b in the dowels 40a, 40b and into the tibia 10 as generally illustrated in FIG. 4. Similar to the pins 34a, 34b, the alignment pins 48a, 48b may include a depth feature 50a, 50b configured to control the depth of the alignment pins 48a, 48b into the bone 10 (i.e., to prevent the alignment pins 48a, 48b from being set too deep or too shallow within the bone 10). The depth feature 50a, 50b may comprise an indicia (e.g., but not limited to, a laser marking, groove, or the like) which may be aligned with the proximal end of the passageway 44a, 44b in the dowels 40a, 40b.

Figure 5:
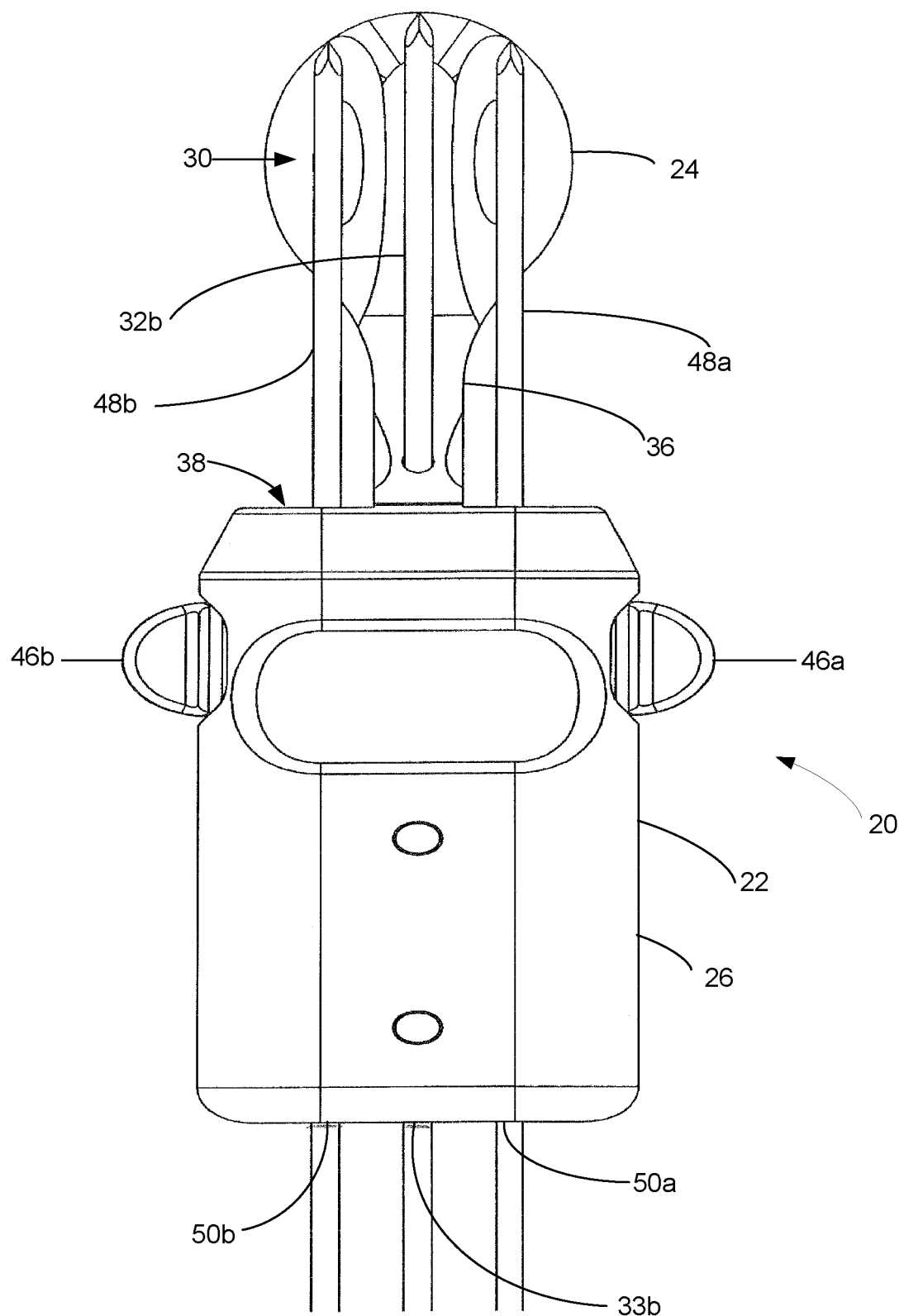
FIG. 5 is a bottom plan view of one embodiment of a drill guide as generally shown in FIG. 4 consistent with the present disclosure.

FIG. 5 is a bottom plan view of the first guide 20 generally illustrating one embodiment of the position of the alignment pins 48a, 48b as well as pin 32b relative to the spoon 24. As can be seen, depth features 50a, 50b, 33b are generally aligned with the respective passageways 44a, 44b, 34b such that the distal ends of the pins 48a, 48b, 32b are generally aligned with the distal perimeter of the spoon 24. As such, the distal ends of the pins 48a, 48b, 32b do not extend beyond the tibial bone 10. It should be appreciates, however, that the position of the distal ends of the pins 48a, 48b, 32b may be disposed shallower (i.e., closer towards the first guide 20).

Figure 6:
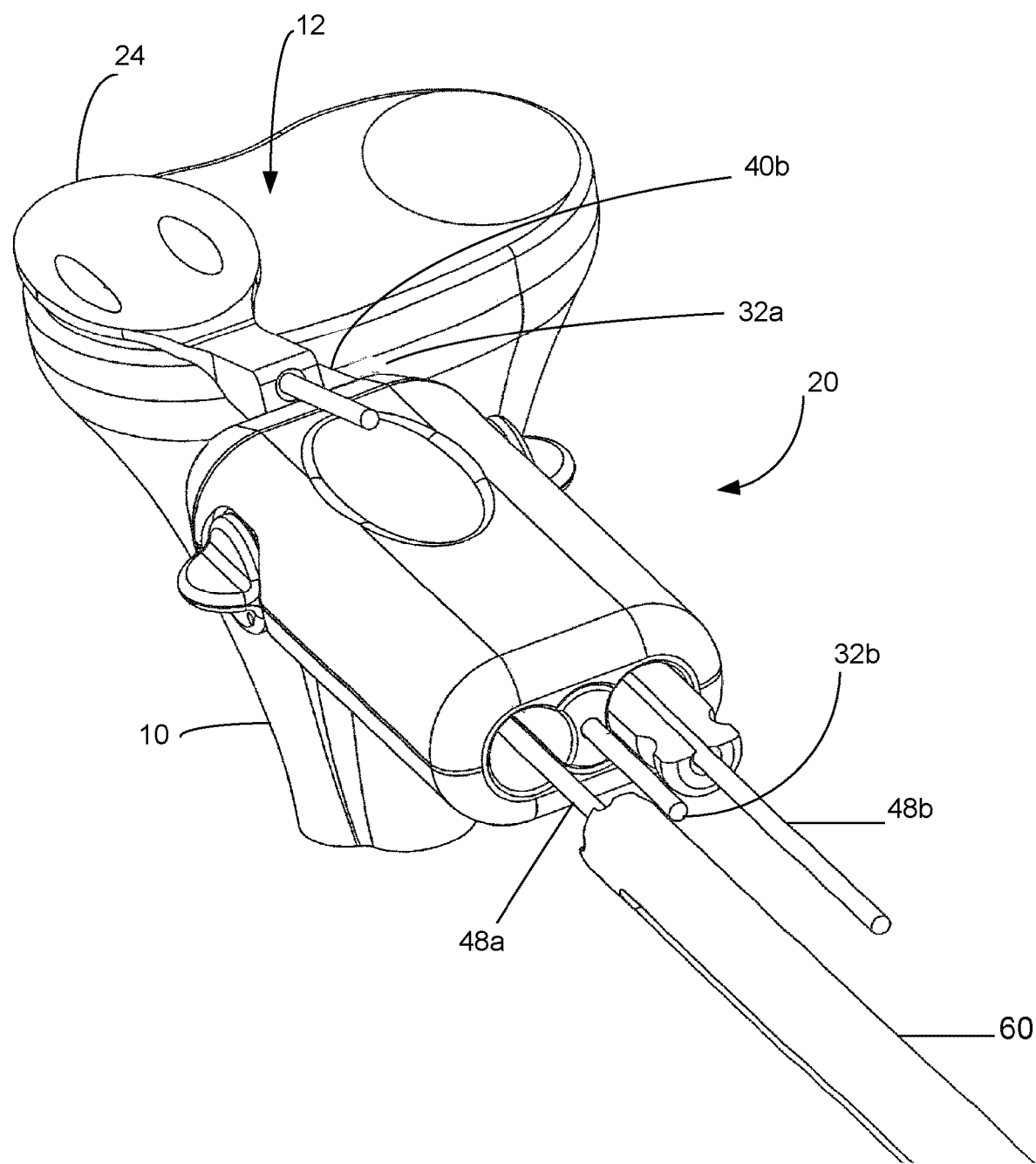
FIG. 6 is a perspective view illustrating a drill bit advanced into the drill guide consistent with the present disclosure.

Once the first guide 20 is secured to the tibia 10, a first and a second truncated cylindrical excision site may be formed in the tibial articular surface 12 and/or bone 10. The first and second truncated cylindrical excision sites may correspond to a projection of the cylindrical core pathways defined by the excision passageways 28a, 28b intersecting with the tibial articular surface 12 and/or bone 10. For example, a dowel 40a may be removed from the excision passageway 28a, leaving the pin 48a remaining as generally illustrated in FIG. 6. A cannulated drill 60 may then be advanced over the pin 48a and through the excision passageway 28a to form a first truncated cylindrical excision site. While dowel 40a is shown removed, the order in which the dowels 40a, 40b are removed may be altered.

Figure 7:
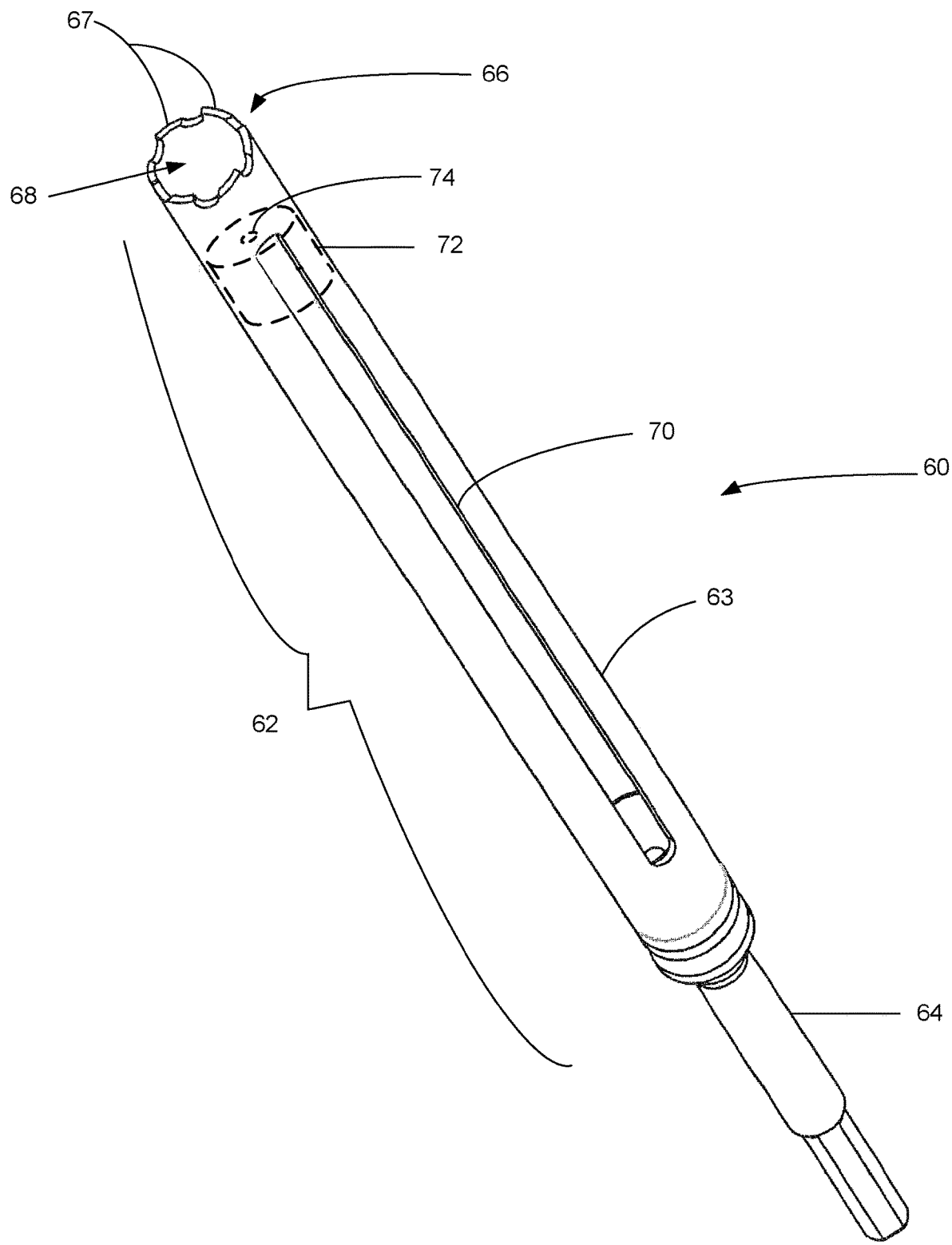
FIG. 7 is a perspective view of one embodiment of a drill bit consistent with the present disclosure.

One embodiment of a cannulated drill 60 is generally illustrated in FIG. 7. The cannulated drill 60 may feature a core drill bit 62 and optionally a shank portion 64. The shank portion 64 may include a multi-faceted proximal end configured to be secured to a drill (e.g., a hand drill, electric drill, pneumatic drill or the like). Alternatively, a proximal end of the core drill bit 62 may be directly coupled to the drill.

The core drill bit 62 may include a cutting surface 66 (for example, comprising a plurality of cutting teeth 67) disposed about a distal end of the barrel 63. The cutting surface 66 may be evenly disposed around the generally circular distal end of the barrel 63. The barrel 63 may include an outer diameter substantially corresponding to the inner diameter of the excision passageway 28a. For example, the core drill 62 may have an outer diameter selected from the range of 8-12 mm, for example, 10-11 mm. The barrel 63 may define a core cavity 68 configured to receive the removed portion of the tibial articular surface 12 and bone 10. As may be appreciated, the only portion of the tibial articular surface 12 and bone 10 that is cut by the core drill bit 60 corresponds to the thickness of the cutting surface 66, which itself is a function of the wall thickness of the barrel 63. As such, these thicknesses may be selected to remove the least amount of material while also providing the necessary rigidity and/or strength to the core drill bit 60.

The core drill bit 62 may optionally feature one or more windows 70 disposed along the length of the barrel 63. The window 70 may allow air, fluid, and cutting chips to exit the barrel 63. In addition, the window 70 may also allow the user to align the core drill bit 62 with the first guide 20 and/or pins to control the depth of the excision site (i.e., the length of the excision site as measured across the tibial articular surface 12). For example, a proximal end of the window 70 may be generally aligned with the opening on the excision passageway 28a to control the depth of the resulting excision site.

The core drill bit 62 may also optionally include a centering bearing 72 configured facilitate alignment of the core drill bit 62 as the core drill bit 62 is advanced into the tibial articular surface 12 and bone 10. The centering bearing 72 may be translatably disposed along the longitudinal axis of the core drill bit 62 and may include a passageway 74 configured to receive the pin 48a. For example, the centering bearing 72 may be initially located near the distal end of the barrel 62. As the core drill bit 62 is advanced within the excision passageway 28a, the pin 48a may be received in the passageway 74 and the centering bearing 72 may translate towards the proximal end as the core is received in the passageway 74.

As the drill bit 60 is advanced through the excision passageway 28a in the first guide 20, a portion of the cutting surface 66 may engage the tibial articular surface 12 and/or the bone 10, thereby forming a truncated cylindrical excision site. Once the drill bit 60 has been advanced through the excision passageway 28a to create the first excision site, the second truncated cylindrical excision site may be formed. For example, the second dowel 40b may be removed and a second drill bit 60 may be advanced through the second excision passageway 28b in a manner similar to that described herein. The first and second drill bits 60 may have the same or different outer diameters.

As discussed herein, the first and the second excision passageways 28a, 28b may be offset relative to each other. Put another way, the first and the second excision passageways 28a, 28b may be separated by a distance generally perpendicular to the longitudinal axes of the first and the second excision passageways 28a, 28b such that the first and the second truncated cylindrical excision sites do not overlap.

Figure 8:
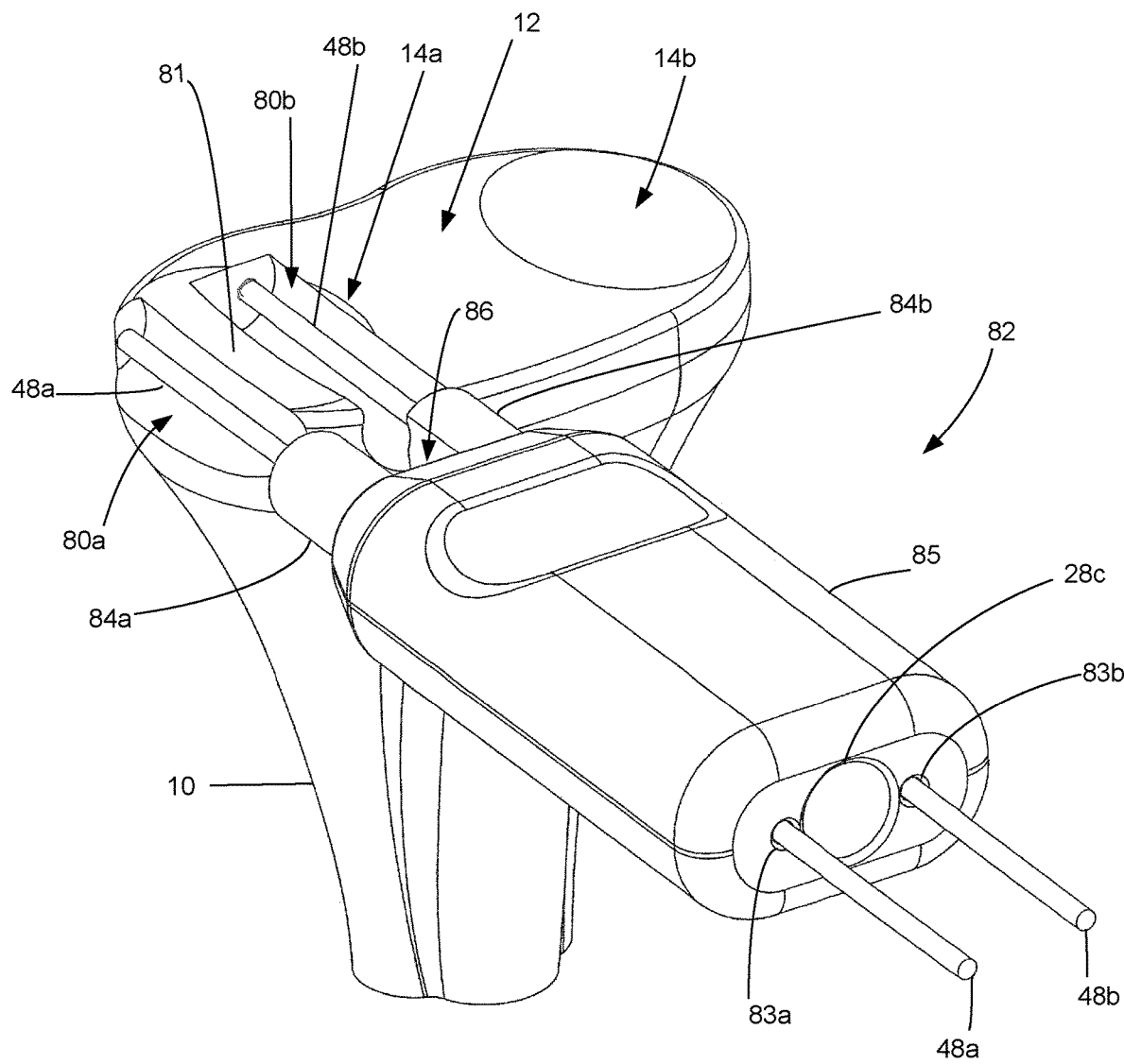
FIG. 8 illustrates one embodiment of a first and second excision site formed on the tibial articular surface and a second drill guide coupled thereto consistent with the present disclosure.

FIG. 8 generally illustrates one embodiment of the first and the second truncated cylindrical excision sites 80a, 80b corresponding to the drill bit 60 and the first and the second excision passageways 28a, 28b. As can be seen, a center section 81 of articular surface 12/bone 10 remains separating the first and the second truncated cylindrical excision sites 80a, 80b. This center section 81 may optionally be removed using second guide/jig 82.

The second guide 82 may comprise one or more alignment passageways 83a, 83b as well as a third excision passageway 28c extending through the body portion 85. The third excision passageway 28c may also define a generally cylindrical core pathway for a drill bit. Once the first and the second truncated cylindrical excision sites 80a, 80b have been formed, the first guide 20 and pins 32a, 32b may be removed and pins 48a, 48b may remain secured to the bone 10. The second guide 82 may then be advanced over the pins 48a, 48b to align the second guide 82 (and in particular the third excision passageway 28c) relative to the articular surface 12 and the center section 81. Optionally, the second guide 82 may feature protrusions 84a, 84b configured to be at least partially received in the first and the second truncated cylindrical excision sites 80a, 80b to further align and secure the position of the second guide 82 and the third excision passageway 28c relative to the articular surface 12/center section 81. The second guide 82 may therefore be advanced along the pins 48a, 48b and the protrusions 84aa, 84b may be received into the first and the second truncated cylindrical excision sites 80a, 80b until at least a portion of the distal face 86 of the second guide 82 generally abuts against the bone 12 and a projection of the third core pathway associated with the third excision passageway 28c partially intersects with the center section 81.

Figure 9:
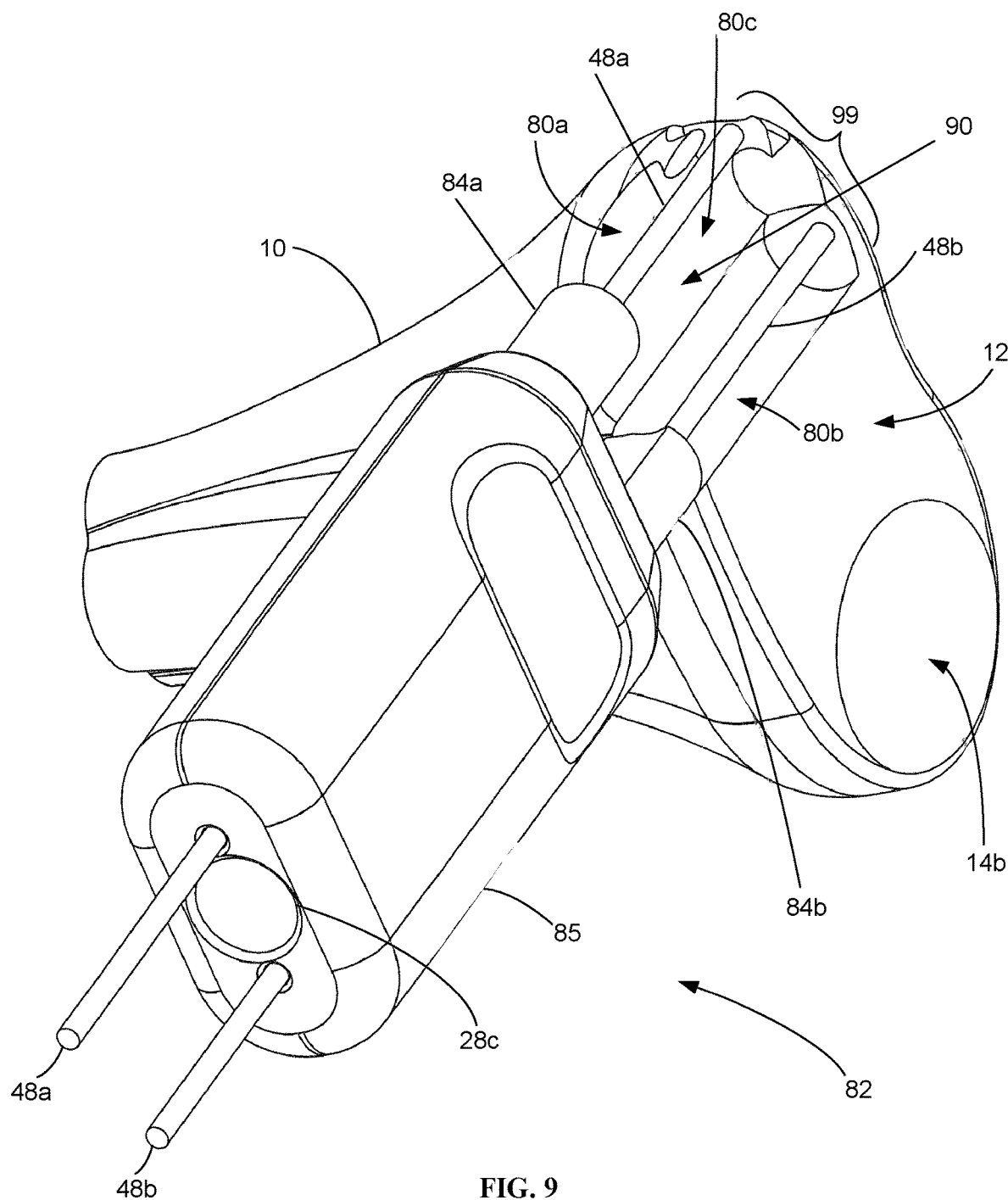
FIG. 9 is a perspective view of one embodiment of a third excision site formed on the tibial articular surface using the second drill guide consistent with the present disclosure.

Once the second guide 82 is aligned with the first and second excision sites 80a, 80b and the pins 48a, 48b, a third drill 60 may be advanced through the third excision passageway 28c extending through the body 85 to remove the center section 81 and form the third truncated cylindrical excision site 80c as generally illustrate in FIG. 9. The third excision passageway 28c may be configured to align the third drill 60 such that the resulting third truncated cylindrical excision site 80c partially overlaps with the first and the second truncated cylindrical excision sites 80a, 80b. For example, the third excision passageway 28c may have a diameter which would partially overlap with the first and the second excision passageways 28a, 28b if the three excision passageways 28a-28c were transposed on each other and aligned with the pins 48a, 48b.

The resulting implant site may therefore comprise the first, second, and third truncated cylindrical excision sites 80a-80c wherein the first and the second truncated cylindrical excision sites 80a, 80b partially overlap with the third truncated cylindrical excision site 80c. The truncated cylindrical excision sites 80a-80c may be centered/revolved around the pins 48a, 48b, 32b and may extend along the articular surface 12 generally along the anterior-posterior plane. For example, the truncated cylindrical excision sites 80a-80c may extend from the anterior face of the tibial articular surface 12 generally towards the posterior face. The implant site may therefore include a base portion 90 comprising three overlapping truncated cylindrical extensions or scallops defined by the three excision passageways 28a-28c. The resulting implant site therefore may generally eliminate/reduce the occurrence of 90 degree cuts and therefore more evenly distribute loads/forces to the bone 10 compared a traditional 90 degree notch cut.

The truncated cylindrical excision sites 80-80c have been illustrated extending partially across the tibial articular surface 12 (i.e., one or more of the truncated cylindrical excision sites 80-80c do not extend completely across the articular surface 12 thus leaving a portion 99 of the tibial articular surface 12 and/or bone 10 remaining). This embodiment may be particularly beneficial since it further minimizes the potential for accidentally damaging the nerve bundle. However, the system and method according to the present disclosure may also allow for one or more of the truncated cylindrical excision sites 80a-80c to extend completely across the articular surface 12 as generally illustrate in FIG. 10. In particular, the system and method according to the present disclosure may be able to accurately enough form the truncated cylindrical excision sites 80a-80c to minimize the potential of damaging the nerve bundle to an acceptable level.

While the system and method has been described having a first and a second guide 20, 82, the system and method may utilize a single guide. For example, the first guide 20 may include alignment dowels (not shown) configured to be advanced and/or secured within the first and second excision passageways 28a, 28b. The alignment dowels may include protrusions 84a, 84b configured to engage the first and second truncated excision sites 80a, 80b as generally described herein. In addition, the guide 20 may include a third excision passageway 28c extending generally along the locking passageway 34b (which itself may be formed in a removable bushing). The alignment dowels may have an outer shape such that the third excision passageway 28c defines a generally cylindrical core pathway for the drill 60.

Figure 11:
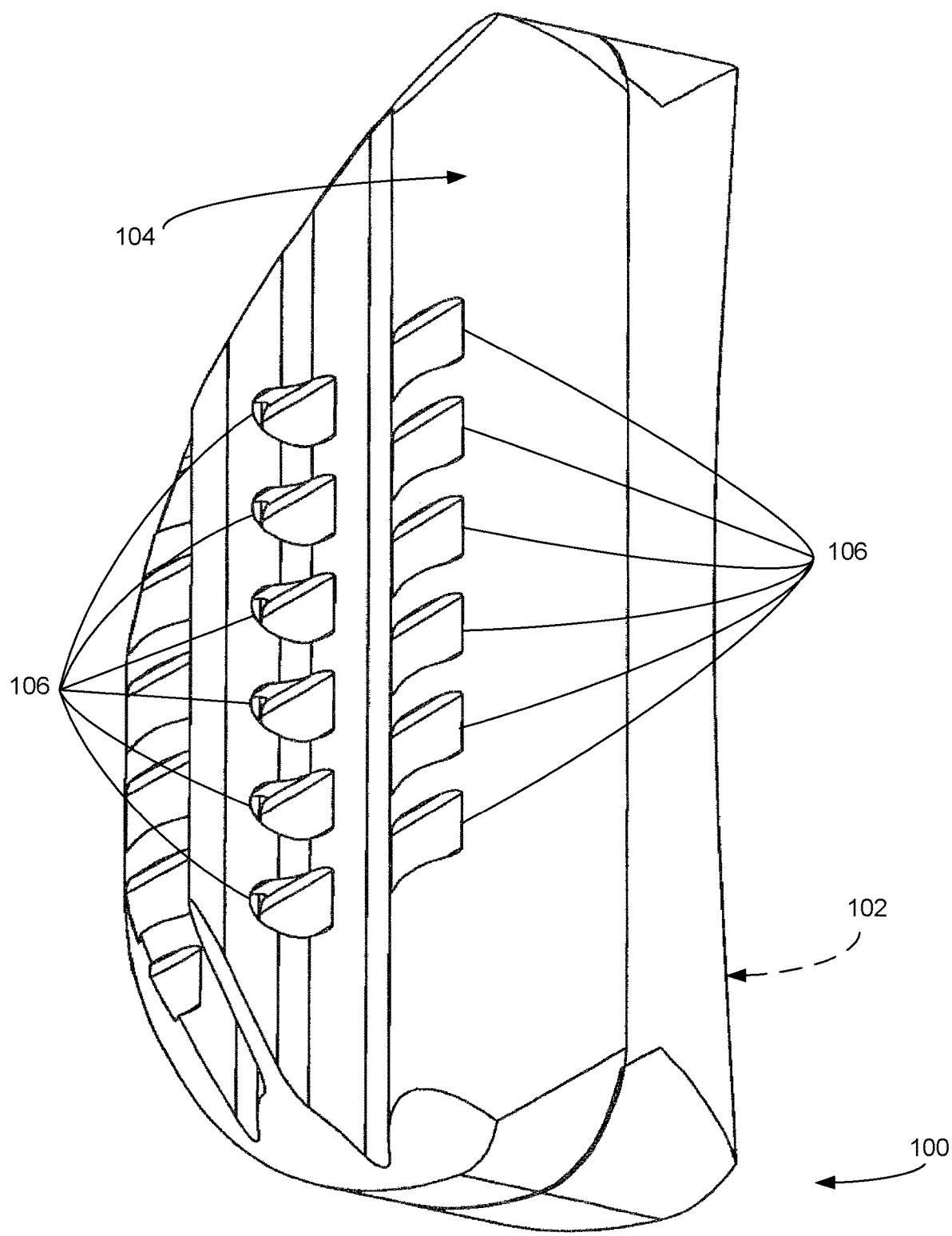
FIG. 11 is a perspective bottom view of one embodiment of an implant consistent with the present disclosure.

Turning now to FIG. 11, one embodiment of an implant 100 consistent with the present disclosure is generally illustrated. The implant 100 may comprise a load bearing surface 102 and a bone facing or distal surface 104. The load bearing surface 102 may have a surface contour/geometry substantially corresponding to the contour/geometry of the removed tibial articular surface 12 proximate the defect 13. The contour/geometry of the load bearing surface may be based on a plurality of measurement take of the patient's tibial articular surface 12, for example, as described in U.S. patent application Ser. No. 10/373,463, filed on Feb. 24, 2003, entitled System and Method for Joint Resurface Repair, which is fully incorporated herein by reference.

The bone facing surface 104 may have an overall contour/geometry generally corresponding to the contour/geometry of the base portion 90 of the three truncated cylindrical excision sites 80a-80c and the removed bone 10. Optionally, the bone facing surface 104 may include one or more relief cavities, pockets and/or cross-cuts 106 configured to enhance securing the implant 100 to the bone 10 within the truncated cylindrical excision sites 80a-80c. The relief cavities 106 may be configured to allow bone regrowth around a portion of the implant 100 and/or promote cement adhesion. As shown, the implant 100 may comprise a generally unitary structure (i.e., the implant 100 may be a solid, one-piece component). For example, the implant 100 may be made from ultra-high molecular weight polyethylene (UHMWPE).

Figure 12:
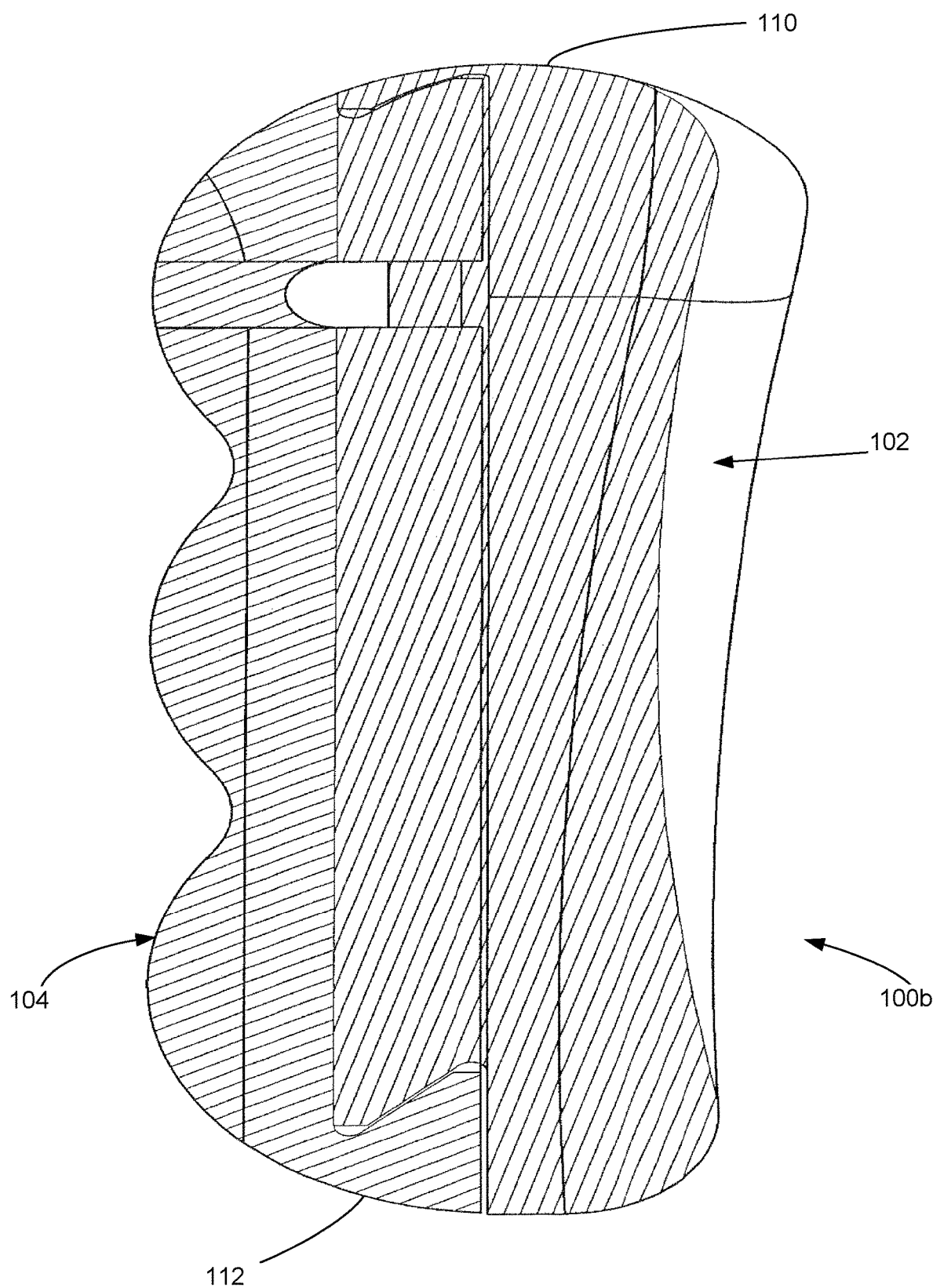
FIG. 12 is a cross-sectional side view of another embodiment of an implant consistent with the present disclosure.

Turning now to FIG. 12, a cross-sectional view of another embodiment of an implant 100b consistent with the present disclosure is generally illustrated. Implant 100b may comprise multiple portions configured to be coupled together, for example, an upper and a lower portion 110, 112. The upper portion 110 may include a load bearing surface 102 as described herein while the lower portion 112 may comprise a bone facing surface 104 as described herein. The upper and lower portions 110, 112 may be configured to be coupled together. For example, the lower portion 112 may be based on the guides 20, 82 used to form the truncated cylindrical excision sites 80a-80c while the upper portion 110 may be based on the contour/geometry of the patient's removed articular surface 12. Put another way, the lower portion 112 may be considered "generic" or common in that it is based on the guides 20, 82 rather than measurements of the patient's articular surface 12 while the upper portion 110 may be selected based specifically on measurements of the patient's articular surface 12.

Figure 13:
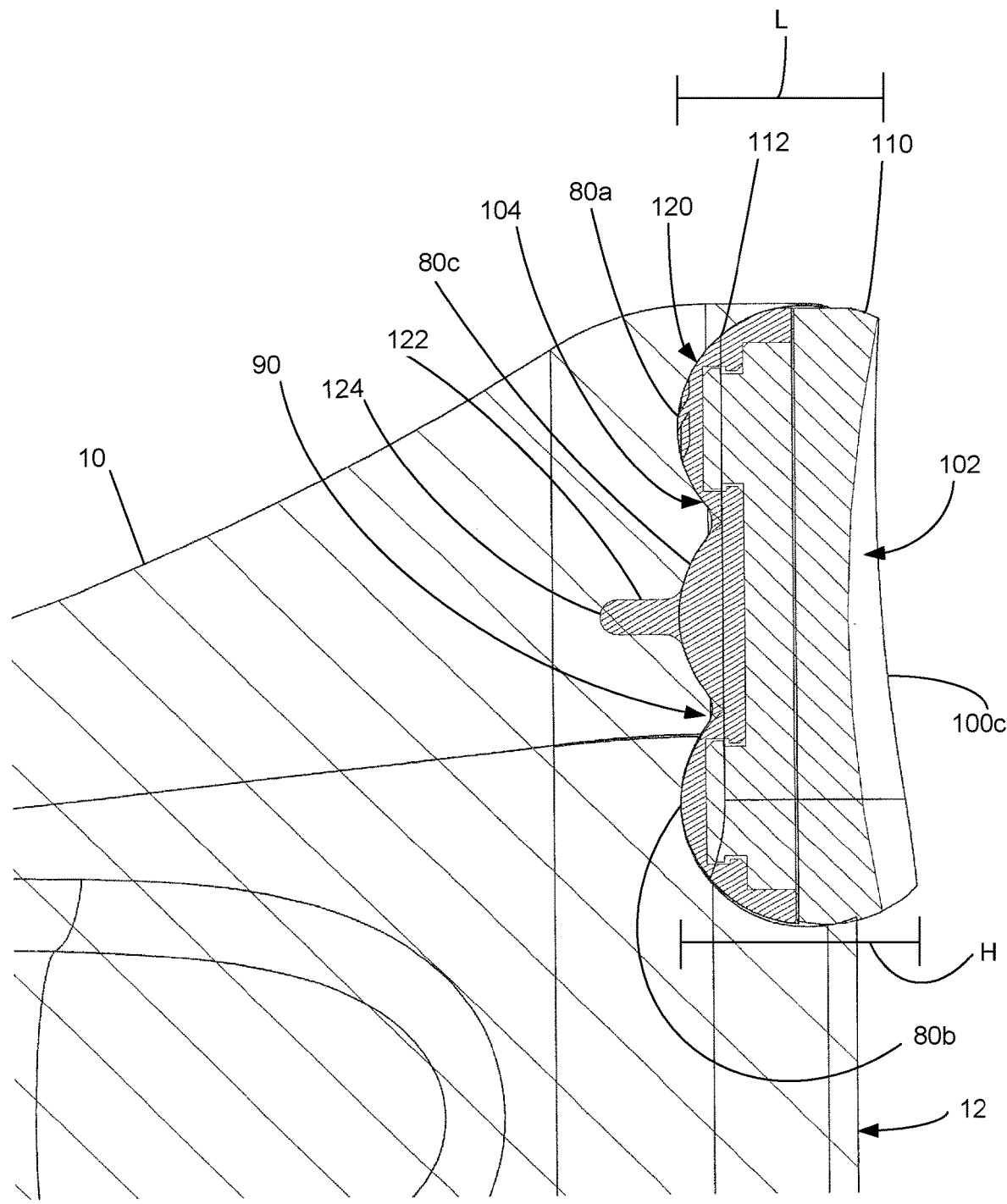
FIG. 13 is a cross-sectional view of yet another embodiment of an implant consistent with the present disclosure.

Turning now to FIG. 13, a cross-sectional view of another implant 100c is shown generally implanted within the implant site 120 formed by truncated cylindrical excision sites 80a-80c. As shown, the bone facing surface 104 of the implant 100c may be generally disposed along the base portion 90 of the truncated cylindrical excision sites 80a-80c while the load bearing surface 102 may be substantially continuous with the surrounding tibial articular surface 12 (i.e., the tibial articular surface 12 adjacent to and abutting the implant 100c). The implant 100c may optionally comprise one or more keels, tails, protrusions or the like 122. The keel 122 may extend generally downwardly from the bone facing surface 104 and away from the load bearing surface 102. The keel 122 may be configured to engage a corresponding notch 124 formed in the base portion 90 of the truncated cylindrical excision sites 80a-80c. While the implant 100c is illustrated having an upper and a lower portion 110, 112, the implant 100 as illustrated in FIG. 11 may optionally include one or more keels 122. The keel 122 may be an integral component of the implant 100 or the lower portion 112 or alternatively may be a separate component coupled thereto.

As may be appreciated from FIGS. 11-13, an implant consistent with at least one embodiment of the present disclosure may have a load bearing surface 102 which is non-planar. While traditional tibial implants have had a generally planar or flat load bearing surface, an implant consistent with at least one embodiment of the present disclosure may have a concaved geometry which may better approximate the geometry of the patient's removed tibial articular surface 12. For example, the implant as shown in FIG. 13 may have a first side (e.g., but not limited to, a medial side) having a height L less than a height H of a second side (e.g., but not limited to, the lateral side).

Figure 10:
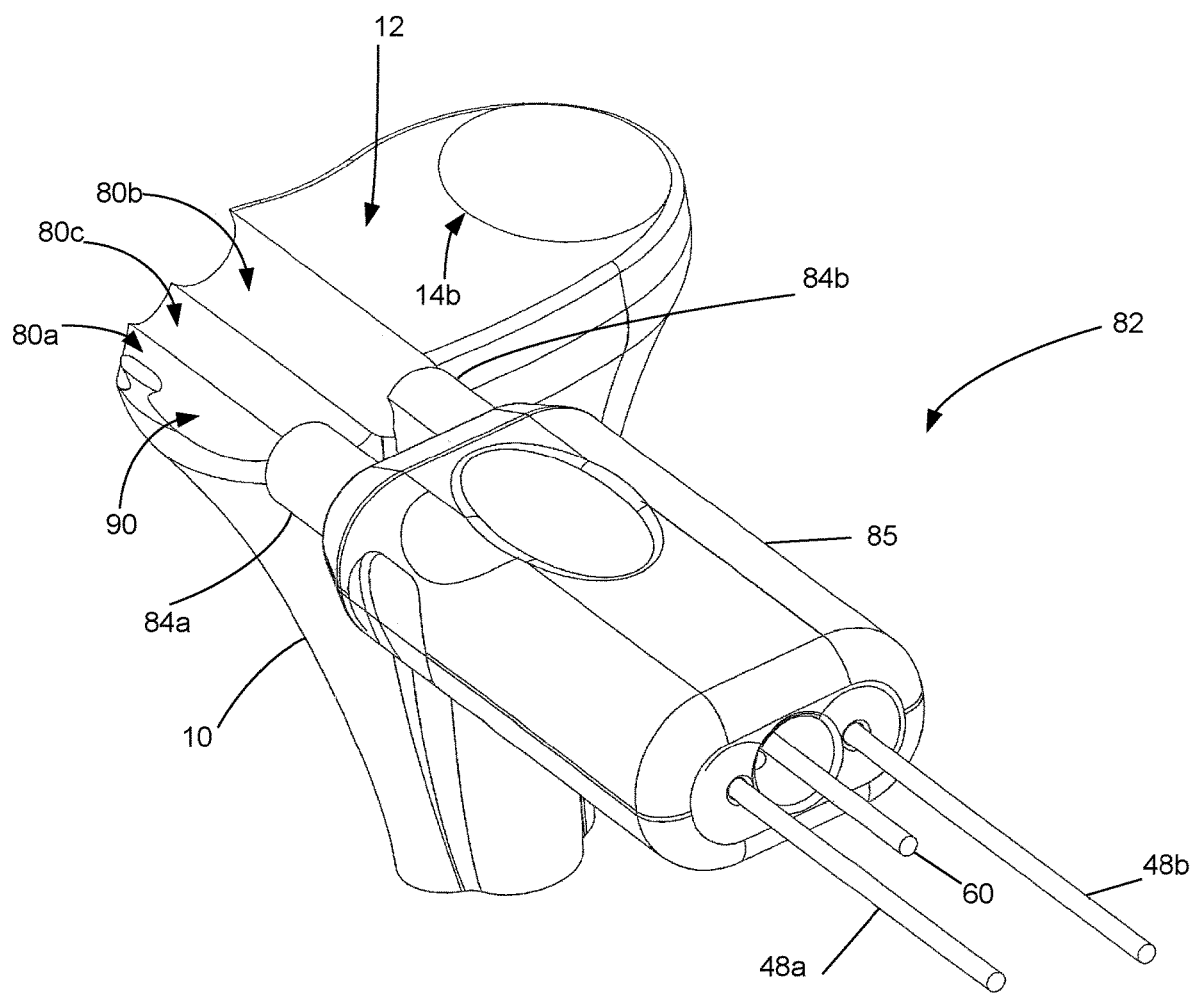
FIG. 10 is a perspective view of another embodiment of a first, second, and third excision site formed on the tibial articular surface using the first and/or second drill guides consistent with the present disclosure.
Figure 14:
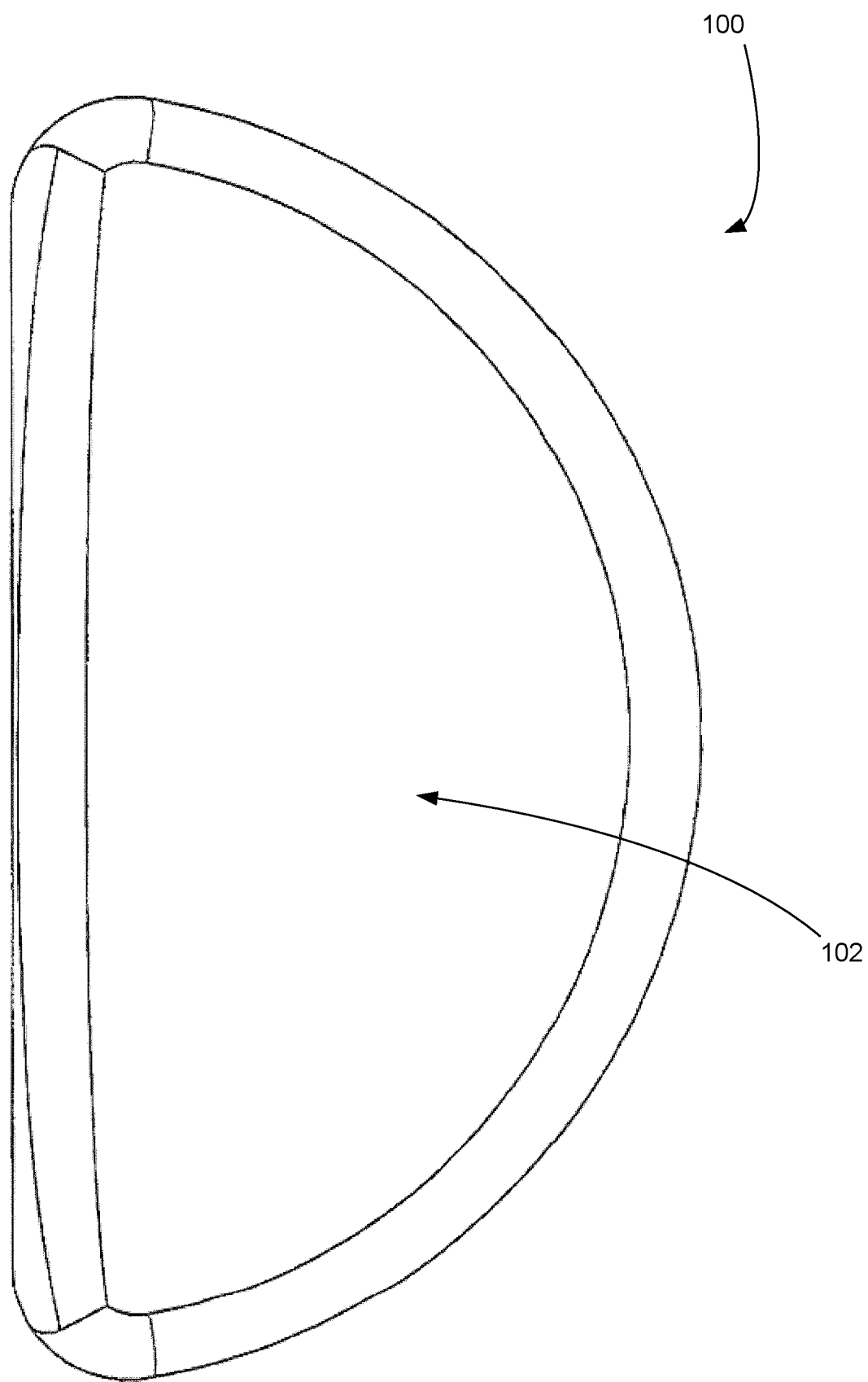
FIG. 14 is a top view of one embodiment of an implant and consistent with the present disclosure.
Figure 15:
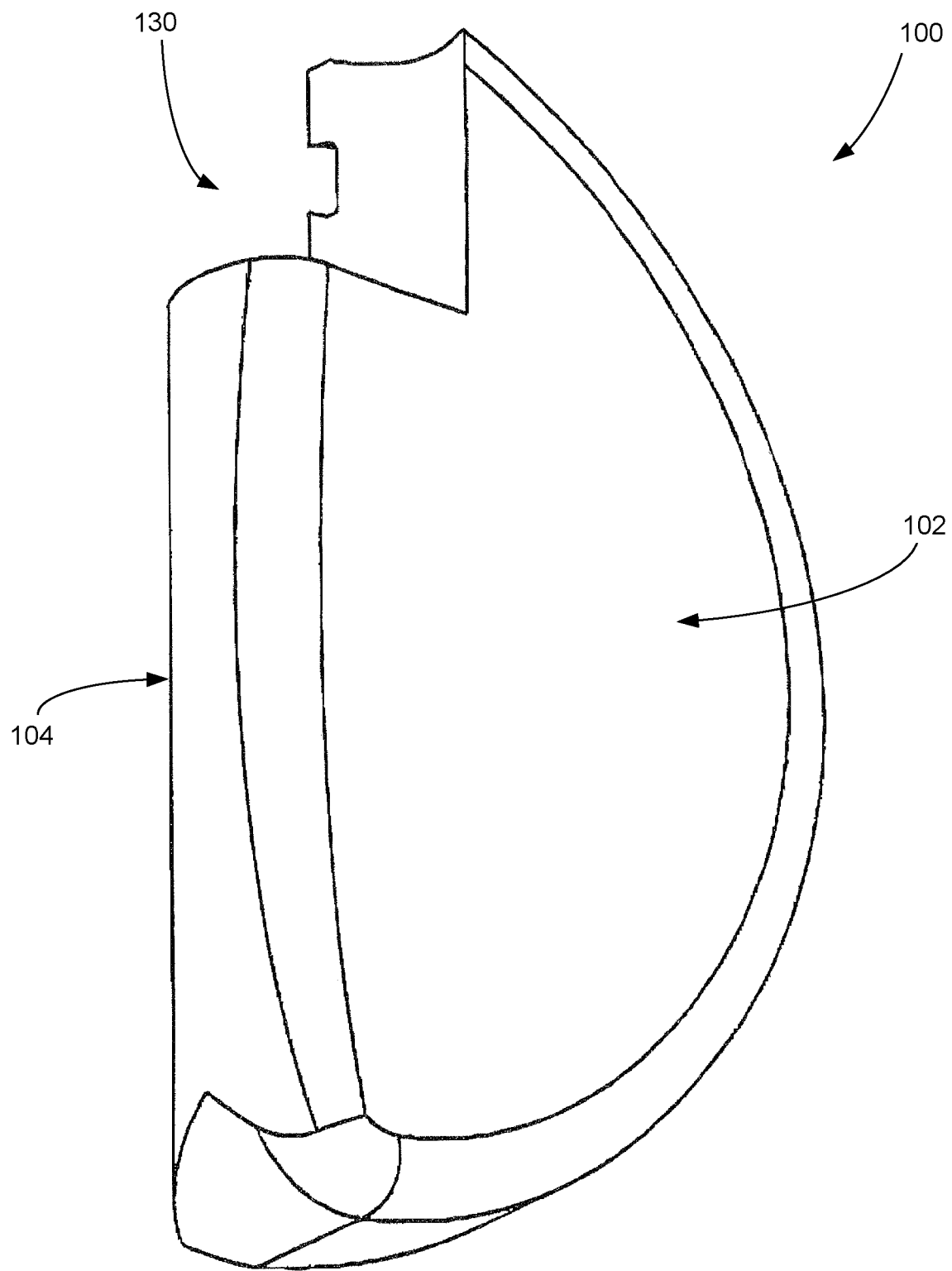
FIG. 15 is a top view of another embodiment of an implant consistent with the present disclosure.
Figure 16:
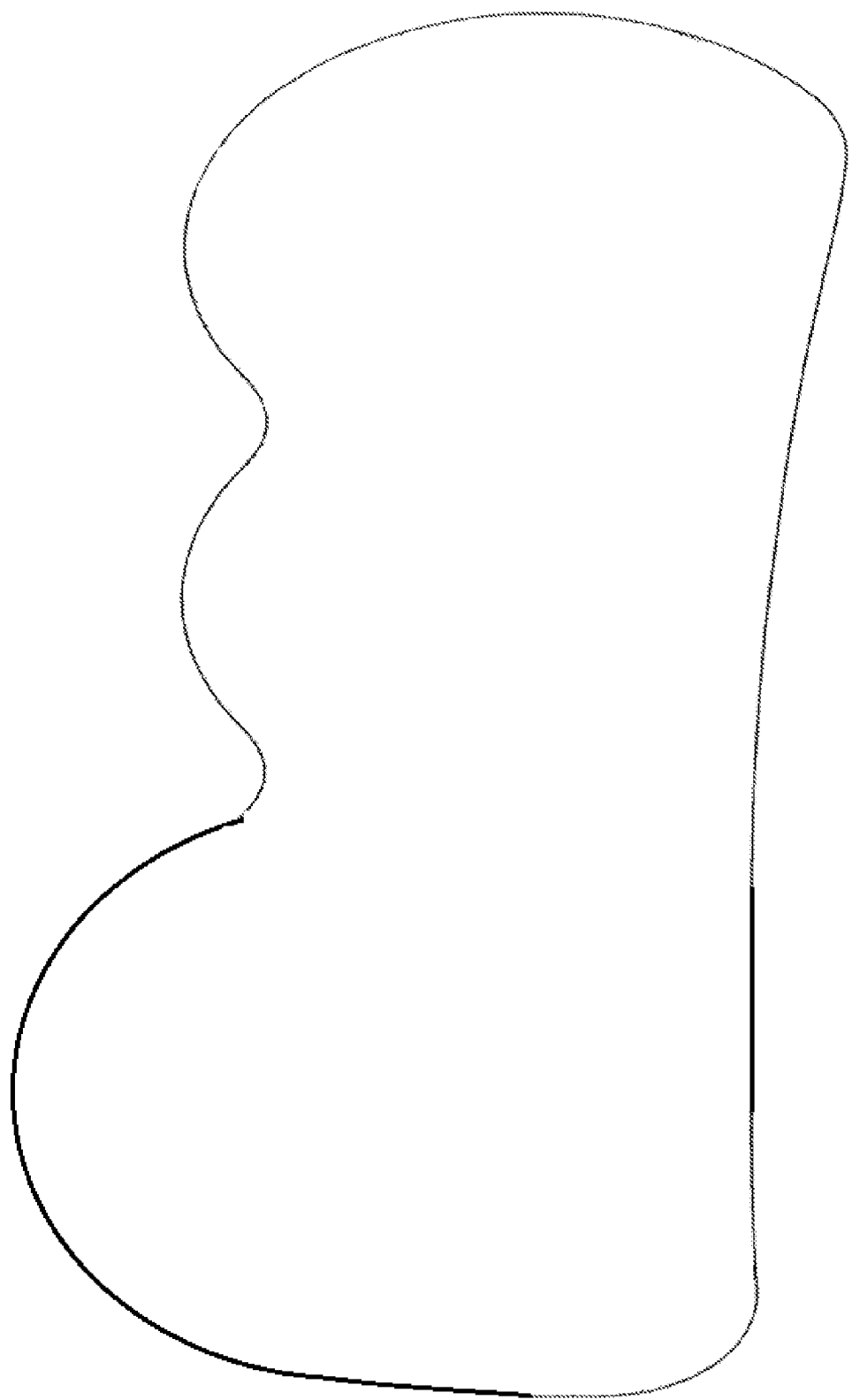
FIG. 16 is a side view of another embodiment of an implant consistent with the present disclosure.

Turning now to FIG. 14, a top view of one embodiments of the implant 100 consistent with the present disclosure is generally illustrated. When viewed from the top side (i.e., when viewing the load bearing surface 102), the implant 100 may have a generally "D" shape. This "D" shape may correspond to an implant site which extends all the way cross the anterior-posterior plane of the articular surface (e.g., as generally shown in FIG. 10). As shown in FIG. 15, the implant 100 may also have a modified or notched "D" shape. In particular, the implant 100 may include a notched region 130 which may correspond to the area 99 of the tibial articular surface 12 proximate to the posterior face of the tibia 10 which is not removed (e.g., as generally shown in FIG. 9). As discussed herein, leaving this portion 99 of the tibial articular surface 12 and/or bone 10 intact may minimize the potential of damaging the nerve bundle 16 (FIG. 1).

According to one aspect, the present disclosure features an implant resection system for preparing an implant site to replace a defect in an articular surface of a first bone. The implant resection system includes a guide configured to be coupled generally perpendicular to the first bone proximate to the defect. The guide includes a body portion defining a plurality of excision passageways. The excision passageways each define a generally cylindrical core pathway configured to extend generally perpendicular to the first bone which partially overlaps with an adjacent generally cylindrical core pathway. A projection associated with each of the plurality of the generally cylindrical core pathways defines a truncated cylindrical excision site extending through a portion of the articular surface. Each truncated cylindrical excision site partially overlaps with at least one adjacent truncated cylindrical excision site.

According to another aspect, the present disclosure features a method for preparing an implant site to replace a defect in an articular surface. The method includes securing a guide to bone proximate the defect. The guide includes a body portion defining a plurality of excision passageways. Each excision passageway defines a generally cylindrical core pathway which partially overlaps with an adjacent generally cylindrical core pathway. The method further includes advancing at least one drill through the plurality of excision passageways along the generally cylindrical core pathways to form a plurality of partially overlapping truncated cylindrical excision sites extending through the articular surface.

While the principles of the present disclosure have been described herein, it is to be understood by those skilled in the art that this description is made only by way of example and not as a limitation as to the scope of the invention. The features and aspects described with reference to particular embodiments disclosed herein are susceptible to combination and/or application with various other embodiments described herein. Such combinations and/or applications of such described features and aspects to such other embodiments are contemplated herein. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

Additional disclosure in the format of claims is set forth below.

What is claimed is:

1. A method for preparing an implant site to replace a defect in a first articular surface of a first bone, the method comprising:
   securing a guide to the first bone at a location proximate to the defect, the guide comprising a body portion defining a plurality of excision passageways, wherein each excision passageway extends through the body portion of the guide defining a generally cylindrical core pathway which partially overlap with an adjacent generally cylindrical core pathway; and
   advancing at least one drill through each of said plurality of excision passageways along said generally cylindrical core pathways to form a plurality of partially overlapping truncated cylindrical excision sites extending through the first articular surface of the first bone;
   wherein securing the guide further comprises the steps of extending an arm outwardly from the body portion, disposing a spoon about a distal end of the arm, advancing the spoon into a space between the first articular surface of the first bone and a second articular surface of a cooperating second bone and advancing at least one locking pin through a locking passageway extending at least partially through the arm thereby securing the arm to the first bone.

2. The method of claim 1, further comprising disposing a first pin through a first excision passageway of the plurality of excision passageways within the guide and at least partially into a first truncated cylindrical excision site of the plurality of partially overlapping truncated cylindrical excision sites formed in the first articulating surface of the first bone, wherein the first excision passageway corresponds with the first truncated cylindrical passageway.

3. The method of claim 2, further comprising disposing a second pin through a second excision passageway of the plurality of excision passageways within the guide and at least partially into a second truncated cylindrical excision site of the plurality of partially overlapping truncated cylindrical excision sites formed in the first articulating surface of the first bone.

4. The method of claim 3, wherein at least one of the first pin and the second pin comprise a depth feature configured to control a depth of the first pin and/or the second pin in the first bone.

5. The method of claim 4, wherein the depth feature comprises an indica selected from a group consisting of a laser marking and a groove.

6. The method of claim 1, further comprising advancing a first alignment dowel and a second alignment dowel within a respective first excision passageway and second excision passageway of the plurality of excision passageways.

7. The method of claim 6, further comprising engaging a protrusion with a first truncated cylindrical excision site or a second truncated cylindrical excision site of the plurality of partially overlapping truncated cylindrical excision sites formed in the first articulating surface of the first bone, wherein the protrusion extends radially from the first alignment dowel or the second alignment dowel.

8. The method of claim 1, further comprising controlling a depth of the drill in the plurality of excision passageways using a depth feature of the drill.

9. The method of claim 1, wherein the drill is selected from a group consisting of a hand drill, an electric drill, and a pneumatic drill.

10. The method of claim 1, further comprising coupling a core drill bit with a shank portion of the drill.

11. The method of claim 10, wherein the core drill bit comprises a centering bearing configured to facilitate alignment of the core drill bit when being advanced into the first articular surface.

12. The method of claim 10, wherein the drill comprises one or more windows disposed along a length of a barrel of the core drill bit.

13. The method of claim 12, further comprising aligning the core drill bit with the guide to control a depth of the excision site.

14. The method of claim 13, further comprising aligning a proximal end of the one or more windows with an opening on a first excision passageway to control the depth of the excision site.

15. The method of claim 1, further comprising abutting a generally convex base portion of the spoon against the first articular surface of the first bone.

16. The method of claim 15, further comprising abutting a generally concaved upper portion of the spoon with a second articular surface of the cooperating second bone.

17. The method of claim 16, wherein the locking passageway is configured to align the at least one pin such that the at least one pin extends into the first bone proximate to a meniscus.

18. The method of claim 1, wherein the first bone is selected from a group consisting of a femur and a tibia, wherein the spoon has a cross-sectional thickness smaller than a distance between the first articular surface and the second articulating surface.

* * * * *